(12) United States Patent
Gao et al.

(10) Patent No.: US 10,613,494 B2
(45) Date of Patent: Apr. 7, 2020

(54) SYSTEMS, METHODS, AND DEVICES FOR DETECTING A VALUE CORRESPONDING TO AN AMBIENT CONDITION AND GENERATING AN ALERT RESPONSIVE TO THE VALUE

(71) Applicant: Honeywell International Inc., Morristown, NJ (US)

(72) Inventors: Yekun Gao, Shanghai (CN); Rongbao Nie, Shanghai (CN); XiaoGuang Zhao, Shanghai (CN); Zhilei Wang, Shanghai (CN)

(73) Assignee: ADEMCO INC., Golden Valley, MN (US)

( * ) Notice: Subject to any disclaimer, the term of this patent is extended or adjusted under 35 U.S.C. 154(b) by 53 days.

(21) Appl. No.: 15/713,925

(22) Filed: Sep. 25, 2017

(65) Prior Publication Data

US 2019/0094823 A1    Mar. 28, 2019

(51) Int. Cl.
| | |
|---|---|
| *G05B 15/02* | (2006.01) |
| *A61B 5/00* | (2006.01) |
| *H04L 12/28* | (2006.01) |
| *G06F 1/16* | (2006.01) |
| *G02C 11/00* | (2006.01) |

(52) U.S. Cl.
CPC ............ *G05B 15/02* (2013.01); *A61B 5/6802* (2013.01); *G02C 11/00* (2013.01); *G06F 1/163* (2013.01); *H04L 12/2823* (2013.01)

(58) Field of Classification Search
CPC ... G05B 15/02; A61B 5/6802; H04L 12/2823; H04W 4/043
See application file for complete search history.

(56) References Cited

U.S. PATENT DOCUMENTS

| | | | | |
|---|---|---|---|---|
| 5,969,604 A | * | 10/1999 | Tice | G08B 17/10 |
| | | | | 340/501 |
| 9,432,612 B2 | | 8/2016 | Bruhn et al. | |
| 9,473,321 B1 | * | 10/2016 | Bazar | H04L 12/2803 |
| 9,576,460 B2 | * | 2/2017 | Dayal | G08B 21/02 |
| 9,934,673 B2 | * | 4/2018 | Hou | G08B 7/06 |
| 9,977,488 B1 | * | 5/2018 | Kong | G06F 1/3293 |

(Continued)

FOREIGN PATENT DOCUMENTS

| | | |
|---|---|---|
| CN | 106646925 A1 | 5/2017 |
| KR | 10-2016-0052487 | 5/2016 |
| WO | 2010/135518 A1 | 11/2010 |

OTHER PUBLICATIONS

English language translation of description for KR20160052487.

(Continued)

*Primary Examiner* — Joseph H Feild
*Assistant Examiner* — Rufus C Point
(74) *Attorney, Agent, or Firm* — Husch Blackwell LLP (57) ABSTRACT

Systems, methods, and devices for generating an alert responsive to a specific value from a sensor of a wearable device connected to a home automation system or a security system are provided. Some methods can include a control panel receiving an alert message from a wearable device indicative of an ambient condition at a current location of the wearable device, and the control panel automatically adjusting a respective output of one or more connected devices with a respective location proximate the current location of the wearable device.

20 Claims, 11 Drawing Sheets

(56) References Cited

U.S. PATENT DOCUMENTS

| | | | |
|---|---|---|---|
| 10,388,085 B2* | 8/2019 | Harish | G01C 21/362 |
| 10,412,811 B1* | 9/2019 | Siminoff | H05B 33/0854 |
| 2006/0226973 A1* | 10/2006 | Catlin | G08B 17/10 |
| | | | 340/539.11 |
| 2007/0100666 A1* | 5/2007 | Stivoric | G05B 1/01 |
| | | | 705/3 |
| 2012/0190949 A1 | 7/2012 | McCombie et al. | |
| 2014/0206954 A1* | 7/2014 | Yuen | A61B 5/02405 |
| | | | 600/301 |
| 2014/0265938 A1 | 9/2014 | Liu | |
| 2014/0340216 A1* | 11/2014 | Puskarich | G08B 17/11 |
| | | | 340/539.11 |
| 2015/0054654 A1* | 2/2015 | Albinali | G08B 21/02 |
| | | | 340/870.01 |
| 2015/0094544 A1* | 4/2015 | Spolin | A61B 5/7275 |
| | | | 600/301 |
| 2015/0223705 A1* | 8/2015 | Sadhu | G01S 19/17 |
| | | | 600/301 |
| 2016/0035205 A1* | 2/2016 | Messenger | A61B 5/746 |
| | | | 340/539.15 |
| 2016/0210834 A1* | 7/2016 | Dayal | G08B 21/02 |
| 2016/0274381 A1 | 9/2016 | Haddadi | |
| 2016/0310049 A1* | 10/2016 | Rowe | A61B 5/1477 |
| 2016/0335917 A1* | 11/2016 | Lydecker | G09B 21/008 |
| 2017/0042486 A1* | 2/2017 | Tsai | A61B 5/0008 |
| 2017/0123391 A1* | 5/2017 | Sinha | G05B 15/02 |
| 2017/0191695 A1* | 7/2017 | Bruhn | G05B 15/02 |
| 2018/0217292 A1* | 8/2018 | Grosse-Puppendahl | |
| | | | G01J 5/0025 |

OTHER PUBLICATIONS

English language translation of bibliographic data and abstract for KR20160052487 (A).

Extended European search report from corresponding EP patent application 18178111.3, dated Dec. 5, 2018.

English language translation of CN patent publication 106646925, dated May 10, 2017.

Constant et al., Pulse-Glasses: An Unobtrusive, Wearable HR Monitor with Internet-of-Things Functionality, 2015 IEEE 12th International Conference on Wearable and Implantable Body Sensor Networks (BSN), pp. 1-5, Jun. 9, 2015.

* cited by examiner

SYSTEMS, METHODS, AND DEVICES FOR DETECTING A VALUE CORRESPONDING TO AN AMBIENT CONDITION AND GENERATING AN ALERT RESPONSIVE TO THE VALUE

FIELD

The present invention relates generally to home automation systems and security systems. More particularly, the present invention relates to systems, methods, and devices for generating an alert responsive to a specific value from a sensor of a wearable device connected to a home automation system or a security system.

BACKGROUND

Known devices for monitoring an ambient condition are configured as standalone units. However, such known devices lack redundancy and integration with larger systems employed in a home. For example, a standalone device for monitoring an ambient condition is only capable of generating an alert signal local to the device itself. This limits the ability of a direct user of the standalone device to intervene in adjusting the ambient condition. Indeed, the alert signal may be ignored.

In view of the above, there is a continuing, ongoing need for improved systems, methods, and devices.

DETAILED DESCRIPTION

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein can include systems, methods, and devices for monitoring an ambient condition and generating an alert responsive to the ambient condition. For example, systems, methods, and devices disclosed herein can include a processor of wearable device that can compare a value corresponding to at least one ambient condition as measured by a sensor of the wearable device to an alert condition stored in a memory of the wearable device and include an alert message in information transmitted to a paired control panel when the value matches the alert condition.

Systems and methods disclosed herein are described in connection with home automation systems or security systems. It is to be understood that such systems can include, but are not limited to systems that include a control panel in communication with a wearable device and a plurality of connected devices or sensors, systems that include a control panel in communication with a central monitoring system, and systems that include a control panel in communication with a mobile device.

Systems and methods disclosed herein are also described in connection with connected devices and sensors (e.g. alarms, light fixtures, etc.). However, it is to be understood that systems and methods disclosed herein are not so limited and can be used in connection with any connected device or internet of things device that can produce a signal perceptible as an alert or a warning.

In accordance with disclosed embodiments, a wearable device disclosed herein can include a sensor that detects a value corresponding to at least one ambient condition relative to the wearable device. A processor of the wearable device can receive the value from the sensor and transmit information to a control panel paired with the wearable device.

In some embodiments, the processor may compare the value to an alert condition stored in a memory of the wearable device. The processor may include an alert message in the information transmitted to the control panel when the value matches the alert condition. The alert condition may include a single value, a set of values, or a range of values specific to the ambient condition being detected by the sensor.

In some embodiments, the wearable device may include an alert button, and the processor may immediately include the alert message in the information when the processor receives a signal indicative of activation of the alert button.

In some embodiments, the wearable device may receive settings or updates for the alert condition from the control panel when the wearable device pairs with the control panel. In some embodiments, the wearable device is authenticated when the wearable pairs with the control panel.

In some embodiments, the sensor may include an ambient light sensor, and the ambient condition detected by the sensor may include an ambient light level. In these embodiments, the alert condition may include a value corresponding to an overly bright level of light, an overly dark level of light, a range encompassing both the overly dark and overly bright levels of light, or a binary set including both the overly dark level of light and the overly bright level of light. The specific value for each level may reflect an ideal value for prolonged reading with minimal eye strain.

In some embodiments, the sensor may be a proximity or distance sensor, and the ambient condition detected by the sensor may include the proximity of the wearable device to an object. The alert condition may include a value corresponding to an ideal distance between the proximity or distance sensor and the object. In some embodiments, the ideal distance can reflect an ideal range for reading.

In some embodiments, the sensor may include an ultraviolet light sensor, and the ambient condition detected by the sensor may include a level of ultraviolet light. The alert condition may include a value corresponding to an ideal maximum or minimum level of ultraviolet light. In some embodiments, the ideal maximum or minimum level can reflect an ideal value for reading.

In some embodiments, the sensor may include a color sensor, and the ambient condition detected by the sensor may include an ambient light color. The alert condition may include a value corresponding to an ideal color of light for a specific activity. In some embodiments, the activity may be reading. For example, it is know that prolonged exposure to blue LED light or white light containing predominantly blue features can result in eye strain. Accordingly, the ideal color of light for reading may include a color other than blue LED light or white light.

In some embodiments, the processor may determine that the value from the sensor corresponds to the wearable device being in a particular operating mode. The processor may then measure the amount of time the wearable device spends in the particular operating mode and include the alert message in the information sent to the control panel when the time measured exceeds a predetermined threshold. For example, the particular operating mode may be a reading position determined by evaluating a combination of ambient conditions as detected by the sensor.

In accordance with disclosed embodiments, systems and methods disclosed herein may include the wearable device, a plurality of connected devices, and a control panel coupled to the wearable device and each of the plurality of connected devices. Each of the plurality connected devices alone or in combination may produce or contribute to a respective first ambient condition at a respective location of each of the plurality of connected devices. The control panel may adjust a respective output of each of the plurality of connected devices to alter the respective first ambient condition.

In some embodiments, the control panel can receive the alert message from the wearable device, identify one or more of the plurality of connected devices having a respective location proximate a current location of the wearable device, and adjust the respective output for the one or more of the plurality of connected devices. The control panel may receive the current location of the wearable device with the information received from the wearable device and retrieve the respective location of the plurality of connected devices from a memory. For example, the wearable device can determine its location in a region using known triangulation techniques or by an integrated tracking system, such as GPS.

In some embodiments, the plurality of connected devices may be assigned to a plurality of zones of the home automation system or the security system based on the respective location of each of the plurality of connected devices. The wearable device may also be assigned to one of the plurality of zones. The control panel may then identify the one or more of the plurality of connected devices with the respective location proximate the current location of the wearable device by identifying which of the plurality of connected devices are assigned to the one of the plurality of zones.

The control panel may adjust the respective output for the one or more of the plurality of connected devices by a specific amount calculated by comparing the value corresponding to the at least one ambient condition to an ideal level for the respective first ambient condition for the one or more of the plurality of connected devices stored in a memory of the control panel. The control panel may also save the value received from the wearable device in the memory and display an analysis of changes in the value over time.

In some embodiments, some of the methods disclosed herein can be completely or partially executed by the processor of the wearable device or by the control panel, for example, when the wearable device sends the value for the sensor directly to the control panel.

The plurality of connected devices may include any type of smart or connected device that can produce an output affecting an ambient condition ad that can be controlled. In some embodiments, the plurality of connected devices may include light fixtures, smart outlets, smart bulbs, wireless speakers, smart stereos, and the like. The control panel may adjust a type of the plurality of connected devices corresponding to the type of ambient condition detected by the sensor. For example, where the sensor is an ambient light sensor, a color sensor, or an ultraviolet light sensor, the control panel may automatically adjust light type ones of the plurality of connected devices to change the ambient light level, light color, or ultraviolet light concentration. Where the sensor is a proximity sensor, the control panel may flash the light type ones of the plurality of connected devices or activate an alarm through noise type ones of the plurality of connected devices to produce a warning signal. The control panel may also activate a local alarm (flashing light, alarm sound, etc.) on the control panel in response to receiving the alert message.

In accordance with disclosed embodiments, the systems and methods disclosed herein may include a mobile device wirelessly paired with the control panel. The control panel may forward the alert message to the mobile device. In some embodiments, the control panel may adjust the respective output of the one or more of the plurality of connected devices responsive to receiving user input from the mobile device. For example, the control panel may receive an alert message indicating the ambient light level is too high, forward the alert message to the mobile device, and lower the light level in response to receiving user input from the mobile device confirming the high level of ambient light or accepting a proposed action to lower the light level. In another example, the control panel may receive an alert message indicating the wearable device is too close to an object, forward the alert message to the mobile device, and initiate a warning signal on or proximate to the wearable device in response to user input from the mobile device confirming the alert message or accepting a proposed action responsive to the warning signal.

Figure 1:
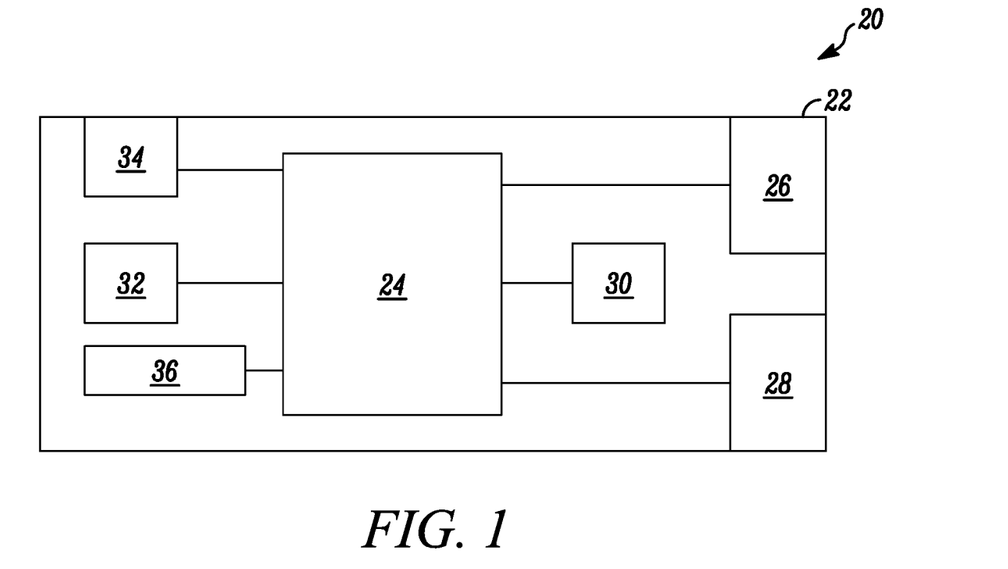
FIG. 1 is a block diagram of a wearable device in accordance with disclosed embodiments.

FIG. 1 is a block diagram of a wearable device 20 in accordance with disclosed embodiments. As shown in FIG. 1, the wearable device 20 can include a housing or enclosure 22 supporting a processor or circuitry 24, a light color sensor 26, a front combination sensor 28, a side combination sensor 30, an alert button 32, a wireless transmitter 34, and an alert indicator 36 (e.g. LED, vibrating motor, etc.).

Figure 2:
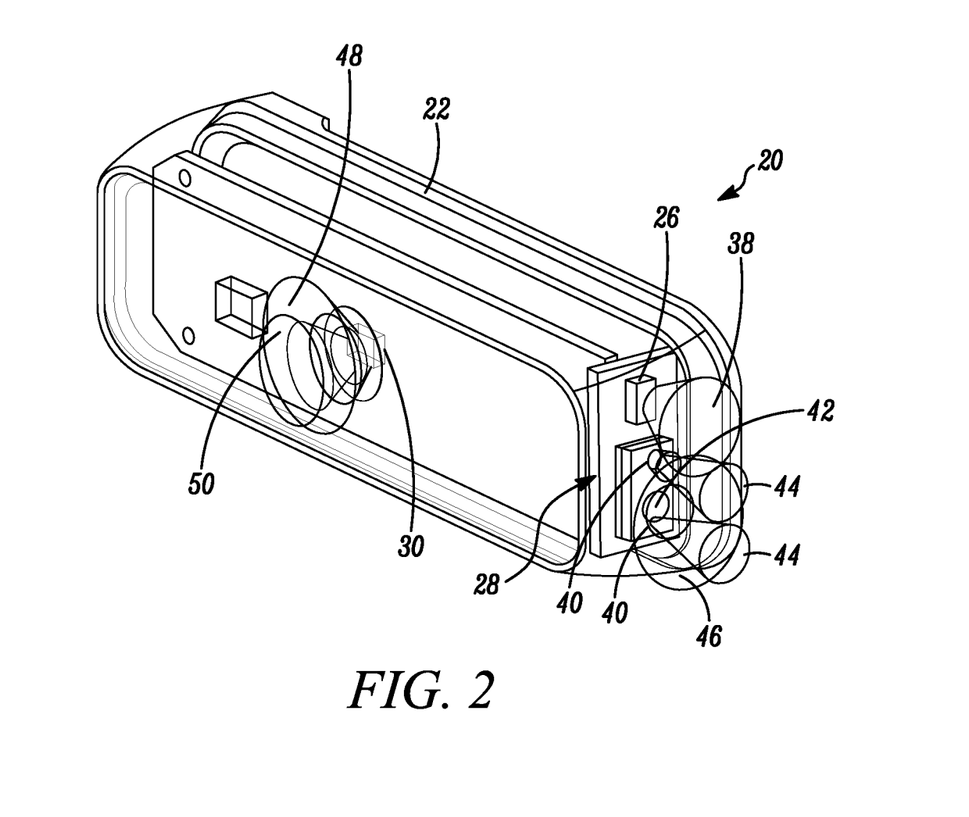
FIG. 2 is a perspective view of a wearable device in accordance with disclosed embodiments.
Figure 3:
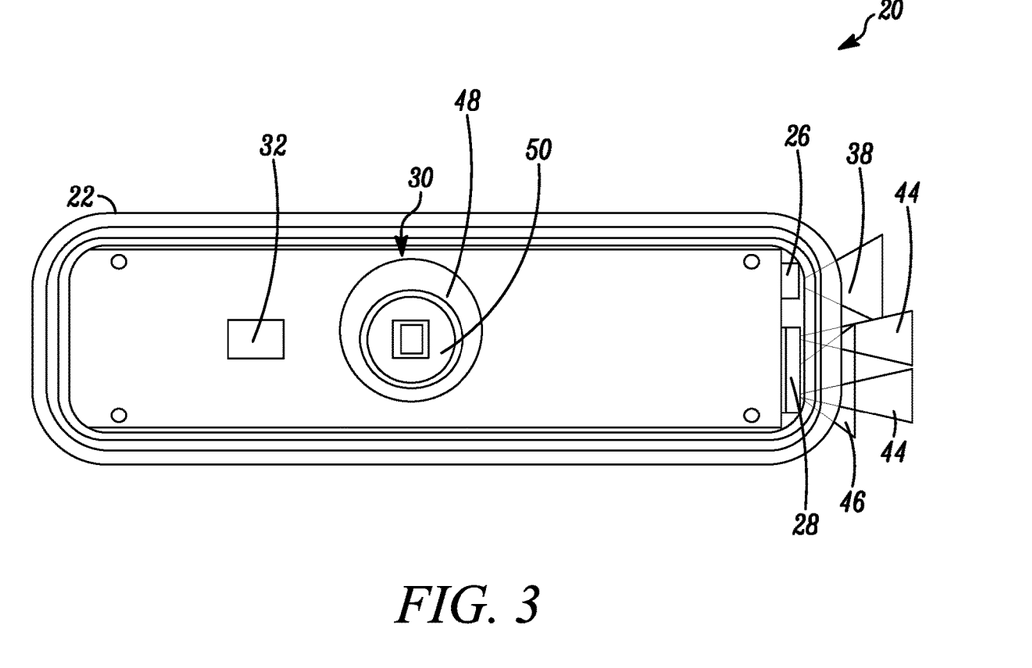
FIG. 3 is a side view of a wearable device in accordance with disclosed embodiments.
Figure 4:
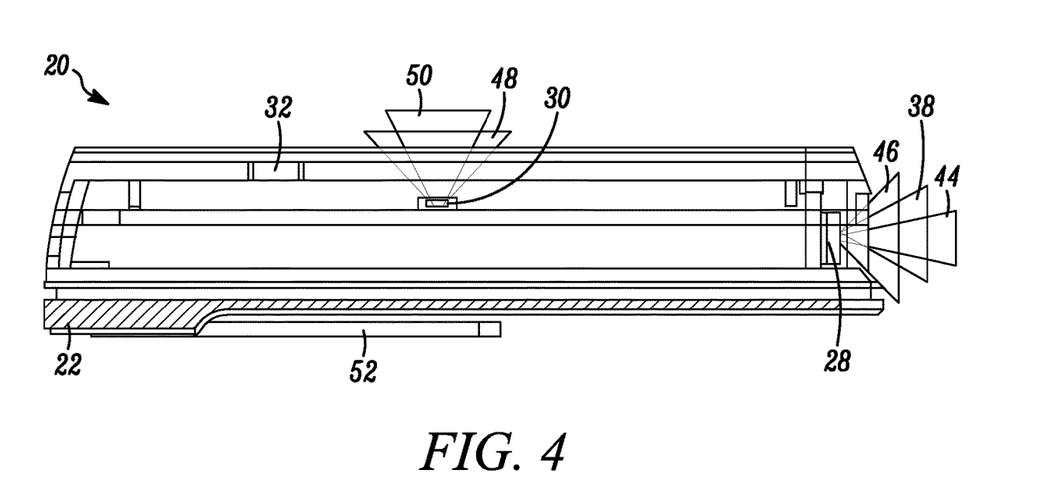
FIG. 4 is a bottom view of a wearable device in accordance with disclosed embodiments.

As shown in FIGS. 2 to 4, the light color sensor 26 and the first combination sensor 28 may reside in a front face of the housing 22, and the second combination sensor 30 may reside on a side face of the housing 22. The light color sensor 26 may determine a value for ambient light color within a color view cone 38 and output the value for ambient light color to the processor 24. The first combination sensor 28 may include proximity sensors 40 and a front ambient light sensor 42. The proximity sensors 40 may determine a value for the wearable device's proximity to an object within the proximity view cones 44 and output the value for the wearable device's proximity to the object to the processor 24. The front ambient light sensor 42 may determine a value for front facing ambient light within a front facing ambient light view cone 46 and output the value for the front facing ambient light to the processor 24. The second combination sensor 30 may include an ultraviolet light sensor and a side ambient light sensor. The ultraviolet light sensor may determine a value for an ambient amount of ultraviolet light present within an ultraviolet view cone 50 and output the value for the ambient amount of ultraviolet light to the processor 24. The side ambient light sensor may determine a value for side facing ambient light within a side facing ambient light view cone 48 and output the value for the side facing ambient light to the processor 24.

In some embodiments, the processor 24 may compare any of the values received from the light color sensor 26, the first combination sensor 28, or the second combination sensor 30 to respective alert conditions corresponding to the ambient conditions measured by sensors. The processor 24 may output an alert message to a control panel via the transceiver 34 when any of the values match the respective alert conditions. In some embodiments, the processor 24 may activate the alert indicator 36 when any of the values match the respective alert conditions.

The alert button 32 may detect user input activating the alert button 32 and may forward a signal indicative of activation to the processor 24. In some embodiments, processor 24 may immediately transmit the alert message to the control panel via the transceiver 34 when the processor 24 receives the signal indicative of the activation of the alert button 32.

Figure 5:
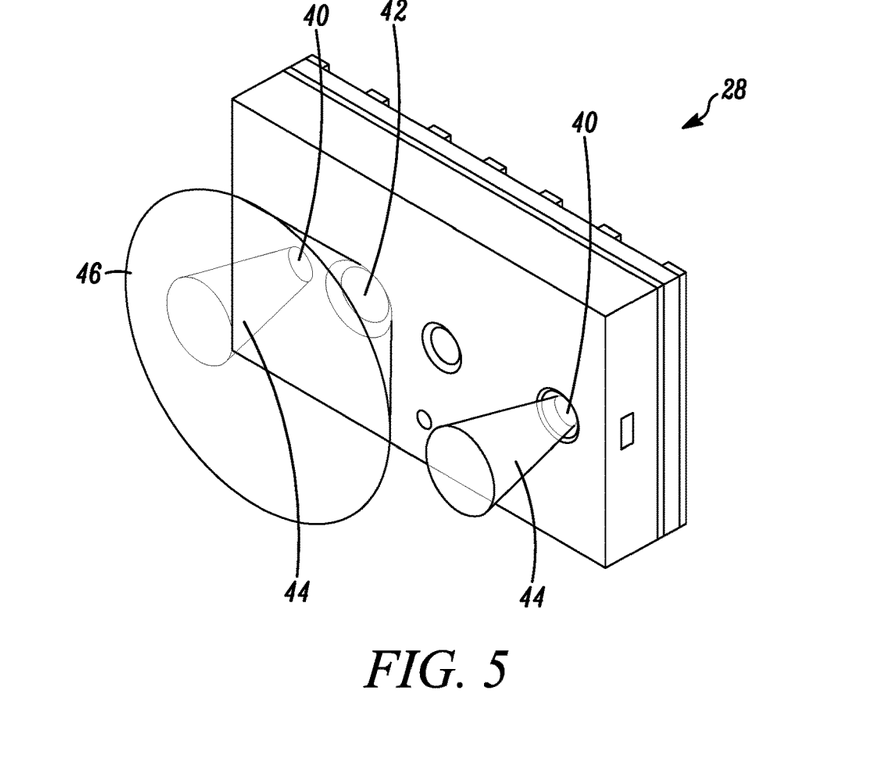
FIG. 5 is a perspective view of a sensor of a wearable device in accordance with disclosed embodiments.
Figure 6:
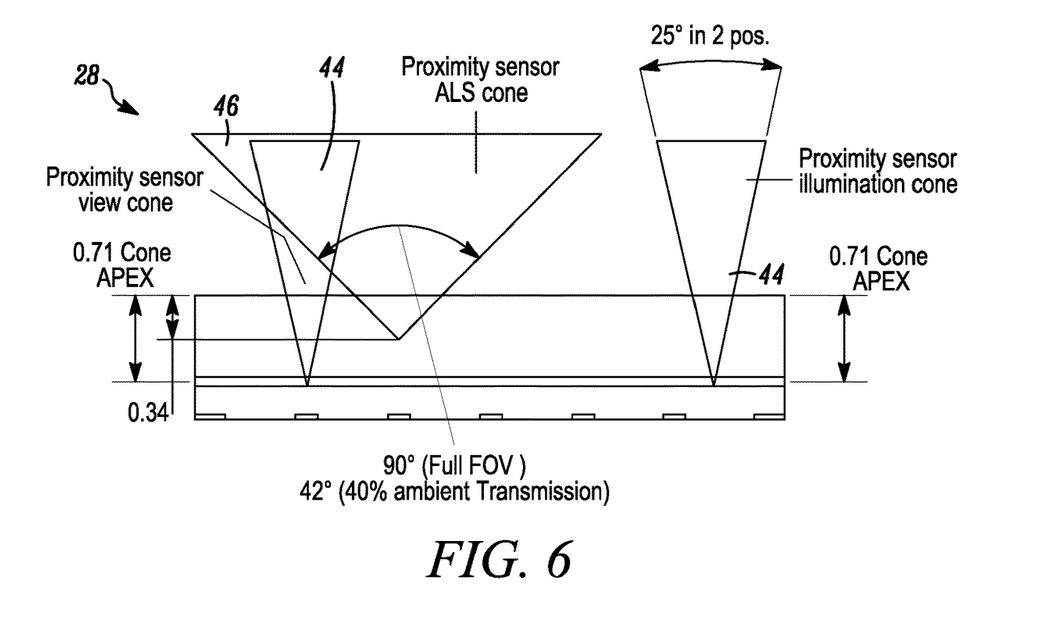
FIG. 6 is a side view of a sensor of a wearable device in accordance with disclosed embodiments.

As shown in FIGS. 5 and 6, the proximity view cones 44 may have a 25 degree field of view plus or minus 12.5 degrees. The front facing ambient light view cone 46 may have a 90 degree field of view plus or minus 45 degrees.

Figure 7:
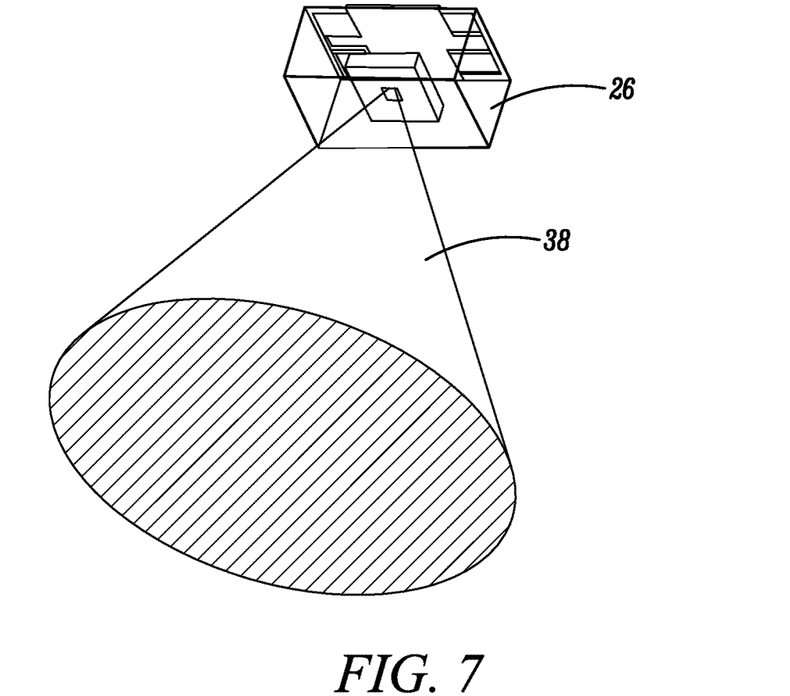
FIG. 7 is a perspective view of a sensor of a wearable device in accordance with disclosed embodiments.
Figure 8:
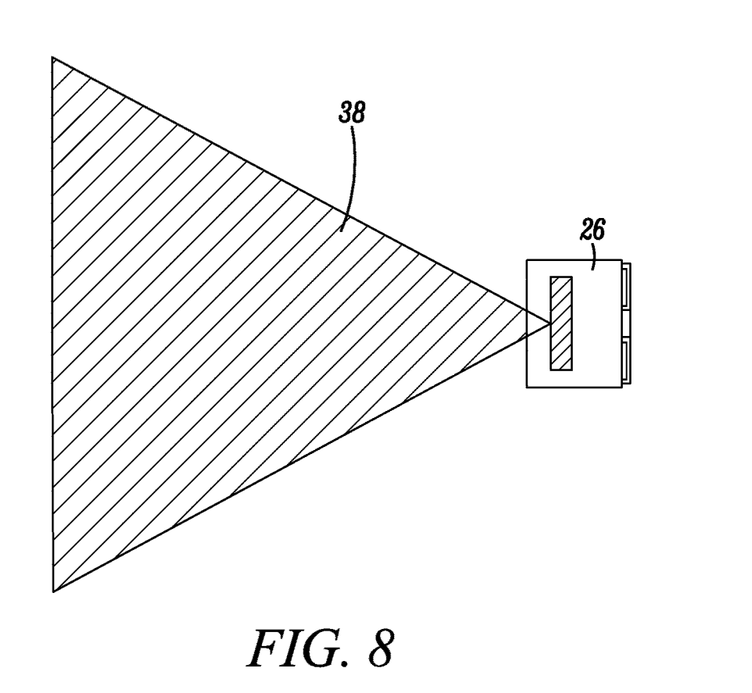
FIG. 8 is a side view of a sensor of a wearable device in accordance with disclosed embodiments.

As shown in FIGS. 7 and 8, the color view cone 38 may have a 90 degree field of view plus or minus 55 degrees. In some embodiments, the color view cone 38 may have a 90 degree field of view plus or minus 27.5 degrees for visual light sensing. A baffle may be included with the light color sensor 26 to limit the effective field angle.

Figure 9:
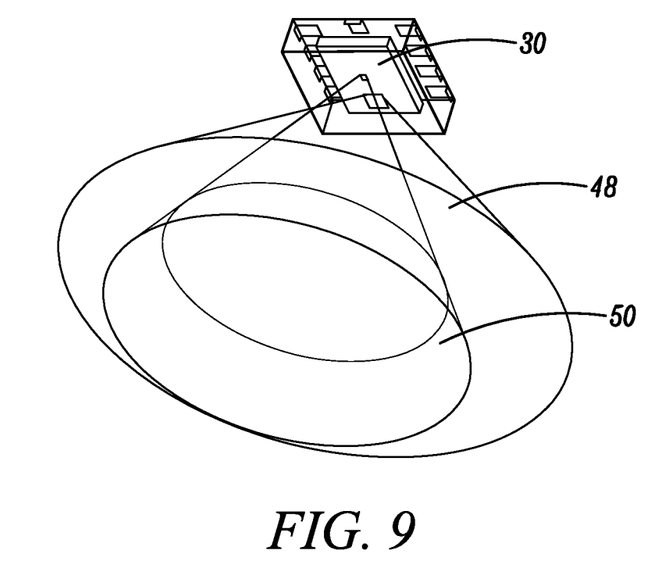
FIG. 9 is a perspective view of a sensor of a wearable device in accordance with disclosed embodiments.
Figure 10:
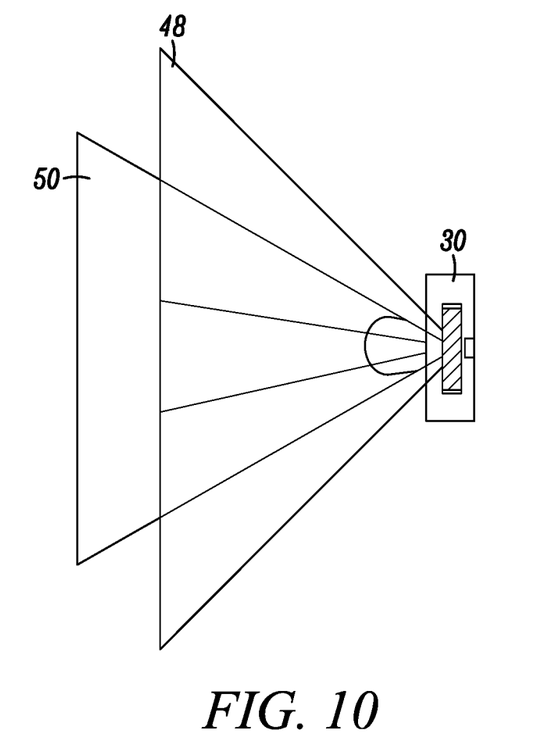
FIG. 10 is a side view of a sensor of a wearable device in accordance with disclosed embodiments.

As shown in FIGS. 9 and 10, the side facing ambient light view cone 48 may have a 90 degree field of view plus or minus 45 degrees. The ultraviolet view cone 50 may have a 60 degree field of view plus or minus 30 degrees.

Figure 11:
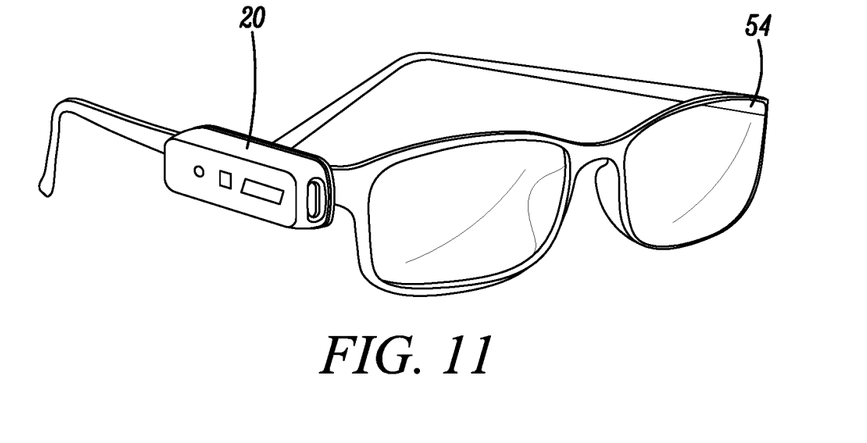
FIG. 11 is a perspective view of a wearable device attached to an object in accordance with disclosed embodiments.

As shown in FIG. 4 and FIG. 11, the housing 22 may include a clip 52 for removably attaching the wearable device 20 to an object 54. As shown in FIG. 11, the object 54 may include a pair of glasses. However, embodiments disclosed herein are not so limited and could include a headband or the like.

Figure 12:
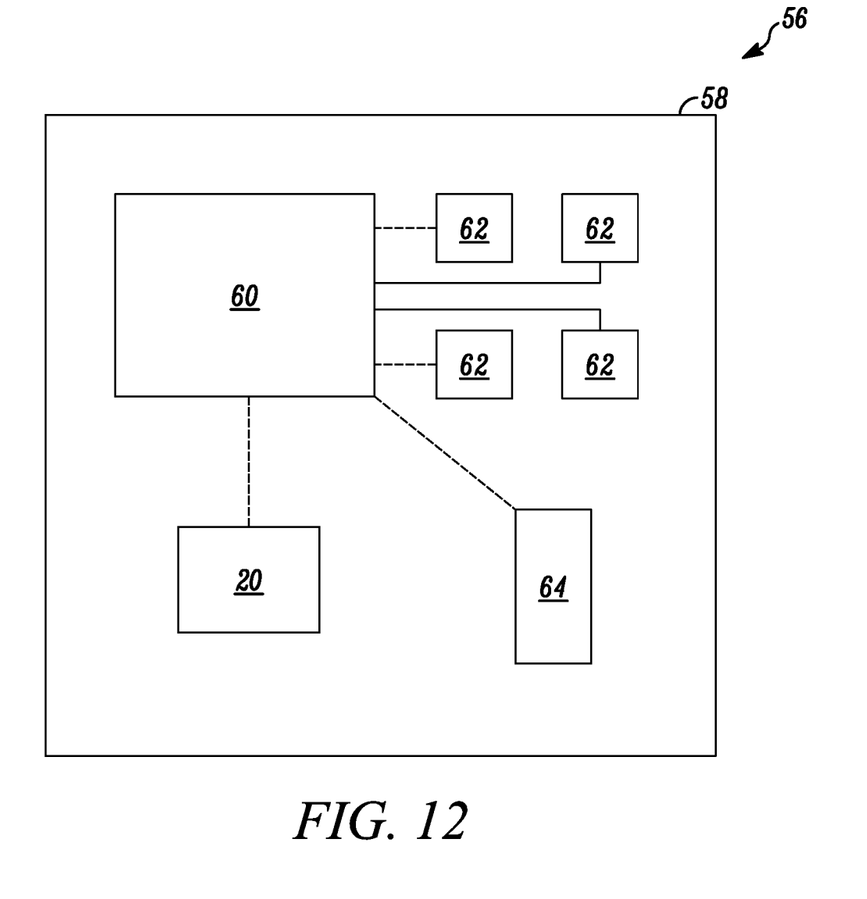
FIG. 12 is a block diagram of a system in accordance with disclosed embodiments.

FIG. 12 is a block diagram of a system in accordance with disclosed embodiments. As shown in FIG. 12, the system 56 (e.g. home automation system, security system, etc.) may be deployed within a region 58 and may include the wearable device 20, a control panel 60, a plurality of connected devices 62, and a mobile device 64. Each of the plurality of connected devices 62 may be coupled to the control panel by a respective wireless or wired connection. The wearable device 20 and the mobile device 60 may be paired or connected to the control panel 60 over a standard wireless connection (e.g. Bluetooth, 802.11, WiFi, radio frequency, infra-red, etc.). As disclosed herein, the control panel 60 may receive the alert message from the wearable device 20 and may change an output of one or more of the plurality of connected devices 62 in response to receiving the alert message. The control panel may also forward the alert message to the mobile device 64.

Figure 13:
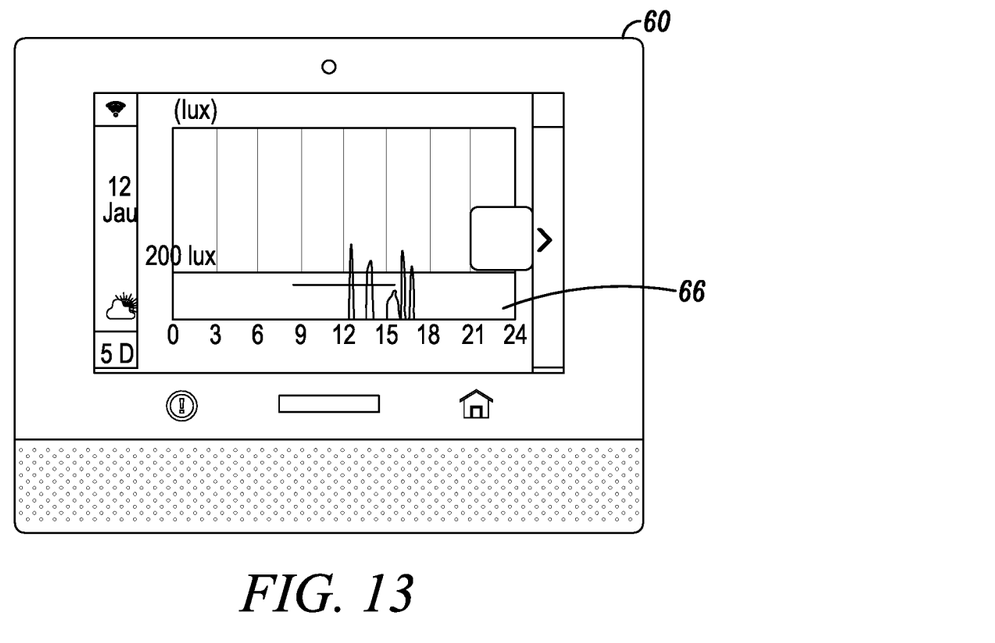
FIG. 13 is a front view of a display of a control panel in accordance with disclosed embodiments.
Figure 14:
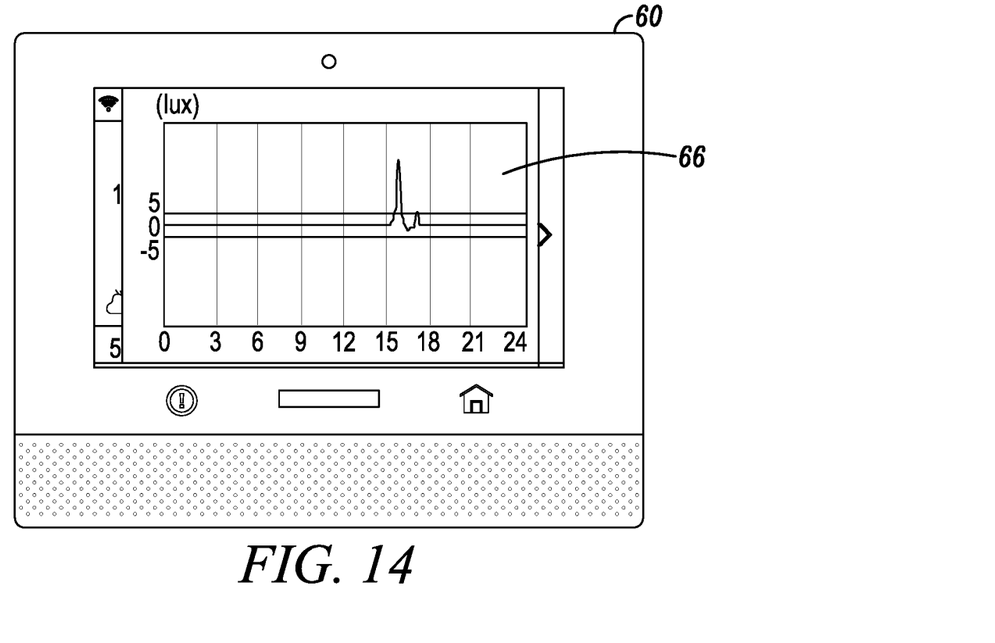
FIG. 14 is a front view of a display of a control panel in accordance with disclosed embodiments.

As shown in FIGS. 13 and 14, the control panel 60 may include a display 66 for displaying an analysis of values collected from the sensors of the wearable device 20 over time.

Figure 15:
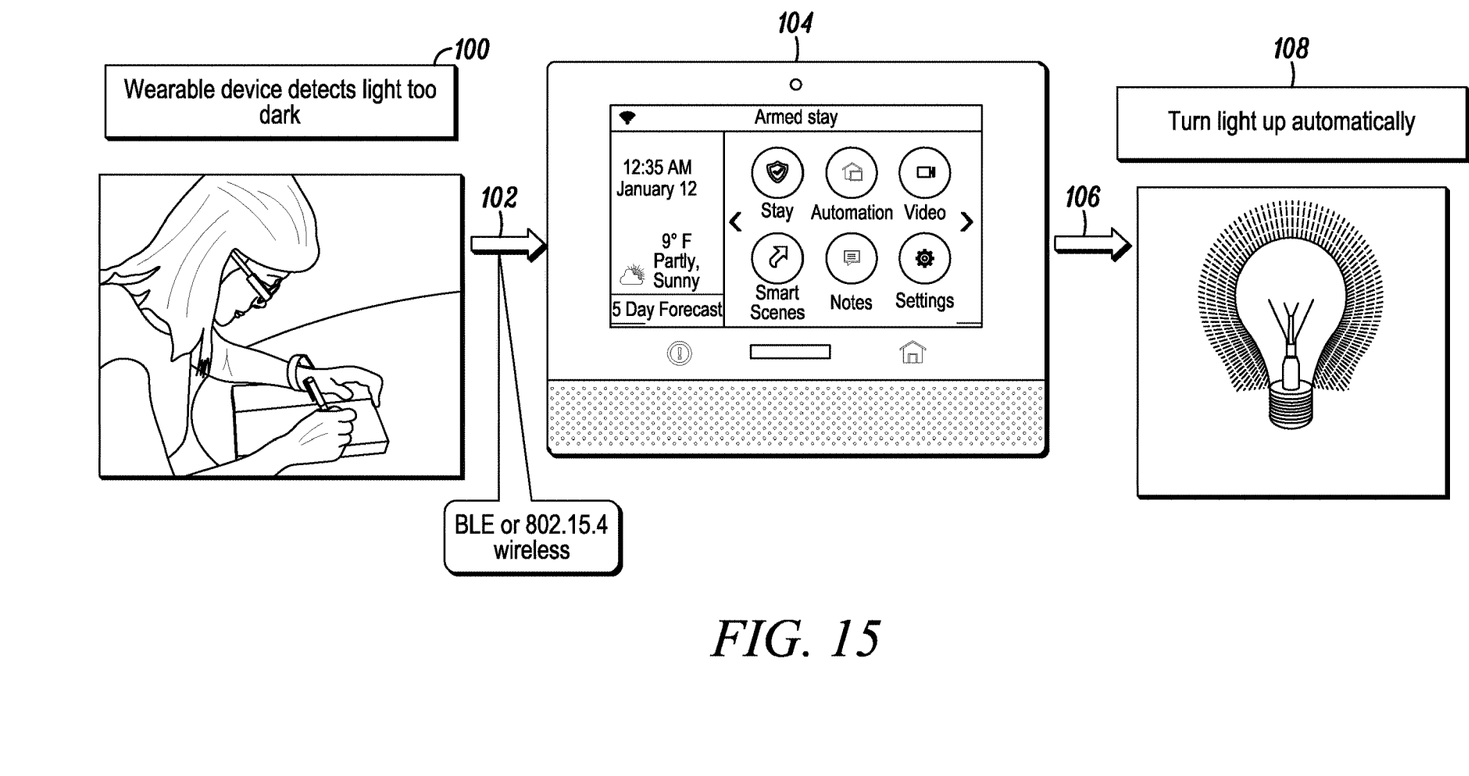
FIG. 15 is a flow diagram of a method in accordance with disclosed embodiments.

FIG. 15 is a flow diagram of a method in accordance with disclosed embodiments. As seen, the wearable device 20 may determine that the ambient light proximate the wearable device 20 is too dark as in 100. The wearable device 20 may forward an alert message to the control panel 60 over a wireless connection, such as Bluetooth, as in 102. The control panel 60 may receive the alert message and identify one or more of the plurality of connected devices 62 that include lights as in 104. The control panel 60 may send a signal to the one or more of the plurality of connected devices identified as in 104 directing the one or more of the plurality of connected devices to increase in brightness as in 106. The one or more of the plurality of connected devices may receive the signal from the control panel 60 and may increase a respective light output as in 108. In some embodiments, the one or more of the plurality of connected devices identified by the control panel 60 can be in proximity to a current location of the wearable device 20.

Figure 16:
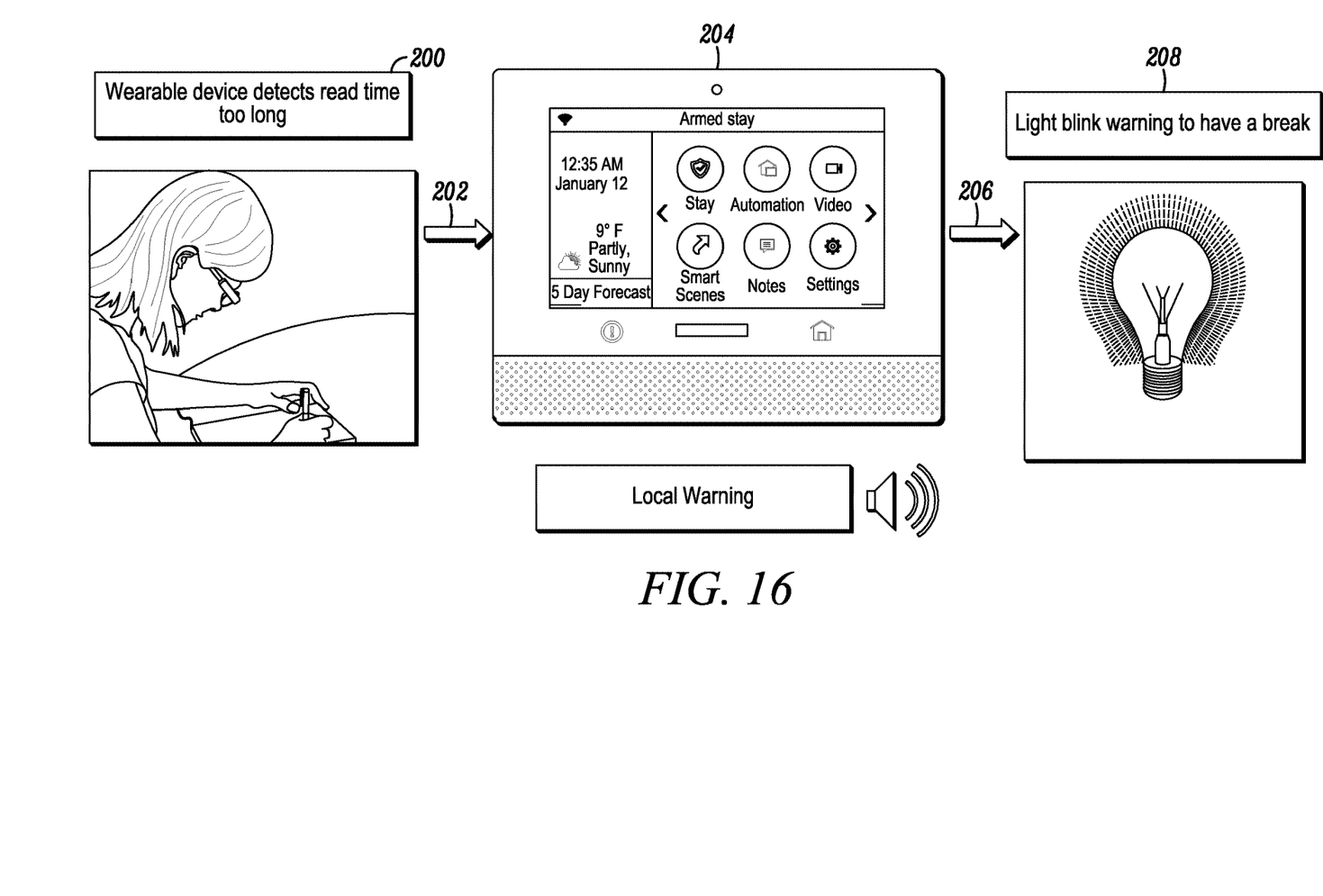
FIG. 16 is a flow diagram of a method in accordance with disclosed embodiments.

FIG. 16 is a flow diagram of a method in accordance with disclosed embodiments. As seen, the wearable device 20 may determine that the wearable device 20 has been in a read time position for too long as in 200. The wearable device 20 may forward an alert message to the control panel 60 over a wireless connection, such as Bluetooth, as in 202. The control panel 60 may receive the alert message, identify one or more of the plurality of connected devices 62 that are in proximity to a current location of the wearable device 60, and activate a local warning alert or alarm at the control panel 60 as in 204. The control panel 60 may send a signal to the one or more of the plurality of connected devices identified as in 204 directing the one or more of the plurality of connected devices to produce a respective warning signal, such as blinking lights, as in 206. Each of the one or more of the plurality of connected devices may receive the signal from the control panel 60 and may initiate the respective warning signal as in 208.

Figure 17:
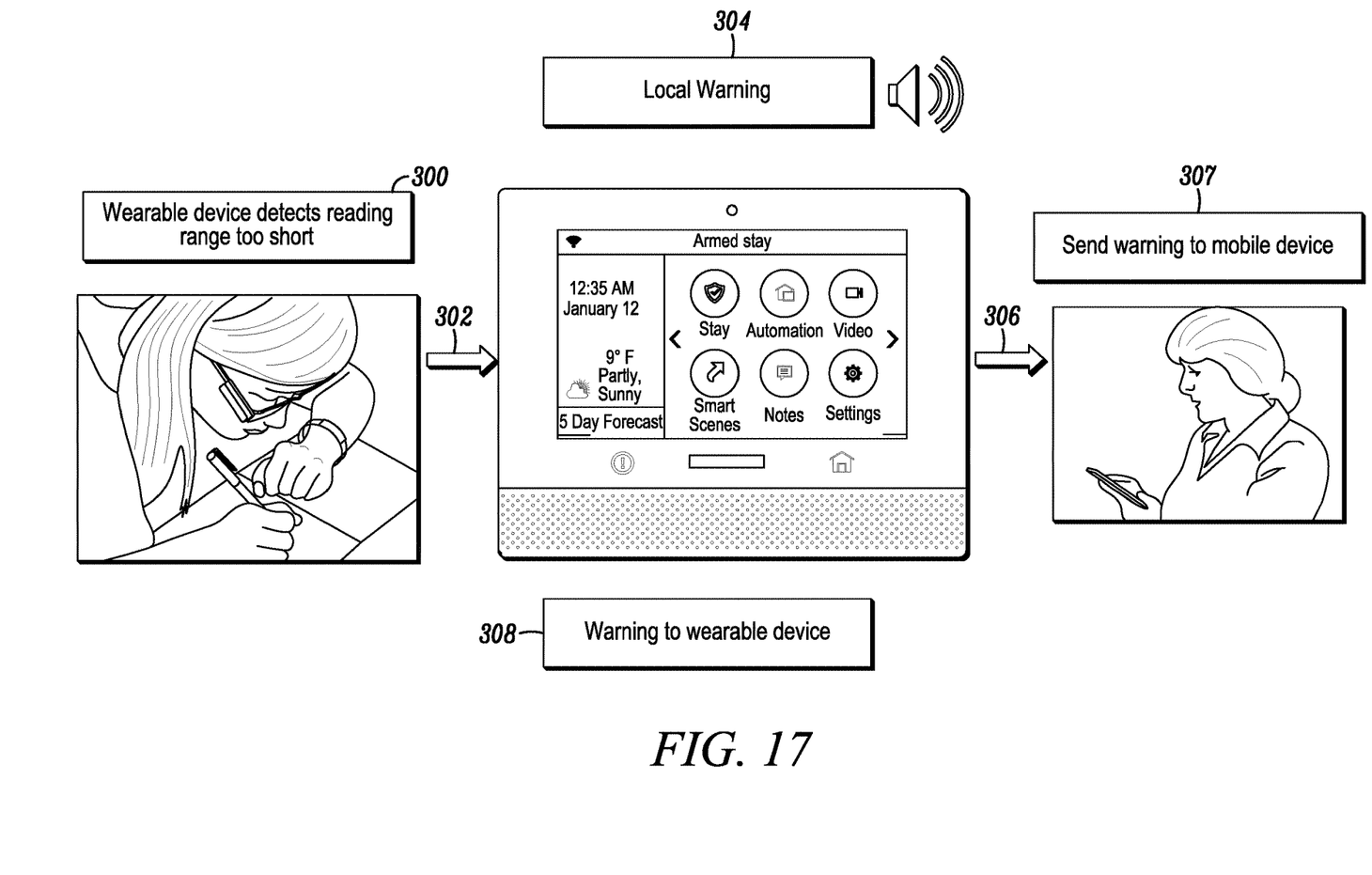
FIG. 17 is a flow diagram of a method in accordance with disclosed embodiments.

FIG. 17 is a flow diagram of a method in accordance with disclosed embodiments. As seen, the wearable device 20 may determine that a reading range of the wearable device 20 is too short as in 300. The wearable device 20 may forward an alert message to the control panel 60 over a wireless connection, such as Bluetooth, as in 302. The control panel 60 may receive the alert message, identify the mobile device 64, and activate a local warning alert or alarm at the control panel 60 as in 304. The control panel 60 may forward the alert message to the mobile device 64 as in 306. The mobile device 64 may receive the alert message from the control panel 60 as in 307. The mobile device may initiate a warning proximate to the wearable device 20 as in 308.

Figure 18:
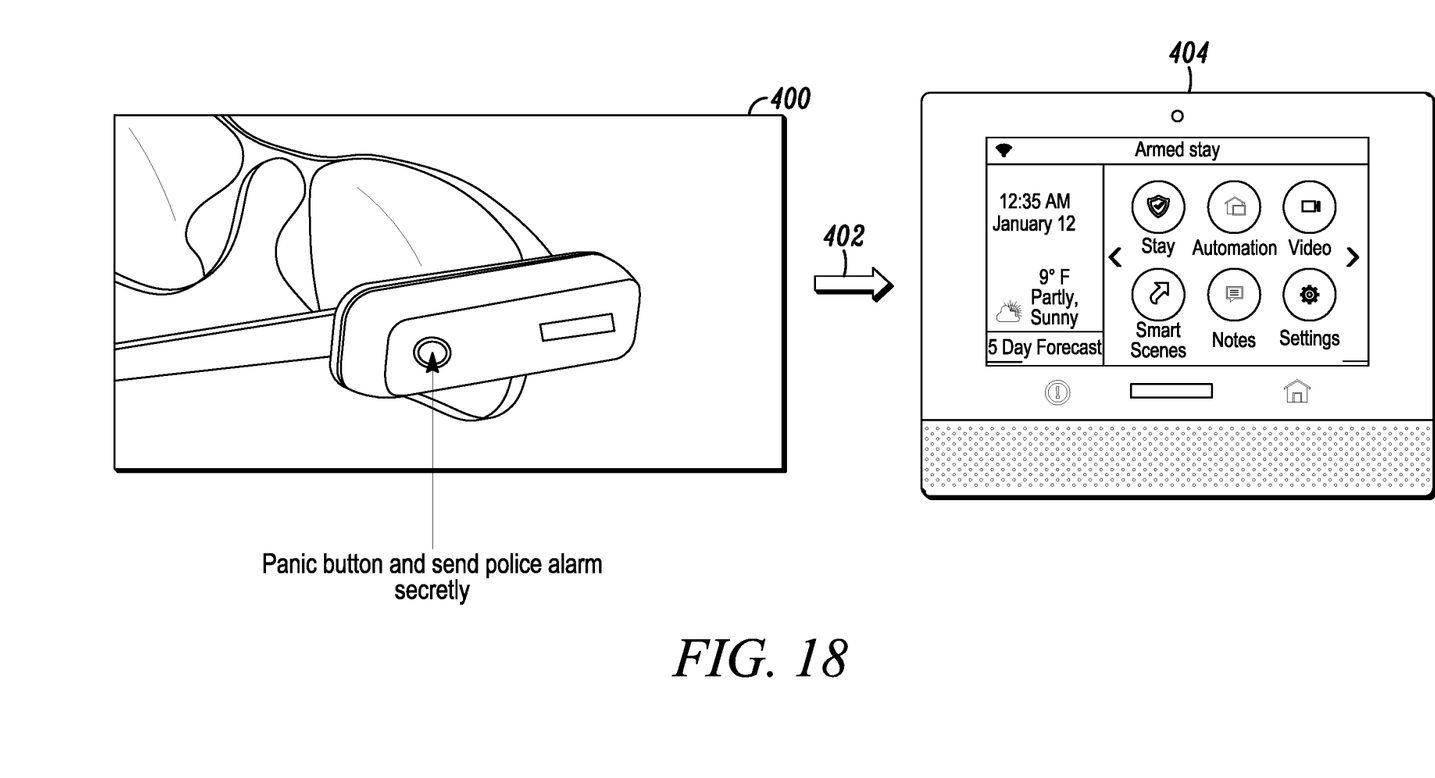
FIG. 18 is a flow diagram of a method in accordance with disclosed embodiments.

FIG. 18 is a flow diagram of a method in accordance with disclosed embodiments. As seen, the wearable device 20 may determine that a panic or alert button has been activated as in 400. The wearable device 20 may forward an alert message to the control panel 60 over a wireless connection, such as Bluetooth, as in 402. The control panel 60 may receive the alert message and trigger an alarm procedure, including contacting outside authorities or a third party monitoring service, as in 404.

Although a few embodiments have been described in detail above, other modifications are possible. For example, the method steps described above do not require the particular order described or sequential order to achieve desirable results. Other steps may be provided, steps may be eliminated from the described flows, and other components may be added to or removed from the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the spirit and scope of the invention.

What is claimed is:

1. A wearable device comprising:
   a first sensor that detects a first value corresponding to a first of a plurality of types of ambient conditions monitored by the wearable device;
   a second sensor different from the first sensor that detects a second value corresponding to a second of the plurality of types of ambient conditions different from the first of the plurality of types of ambient conditions;
   an alert indicator;
   a transceiver; and
   a processor coupled to the transceiver, the first sensor, and the second sensor,
   wherein the processor wirelessly pairs the wearable device with a control panel remote from the wearable device through the transceiver,
   wherein, when the processor receives the first value from the first sensor or the second value from the second sensor, the processor transmits the first value or the second value to the control panel,
   wherein the processor compares the first value to a first alert condition for the first sensor stored in a memory of the wearable device,
   wherein the processor compares the second value to a second alert condition for the second sensor stored in the memory,
   wherein, when the first value matches the first alert condition, the processor transmits an alert message and a first indication of the first of the plurality of types of ambient conditions to the control panel and activates the alert indicator, and
   wherein, when the second value matches the second alert condition, the processor transmits the alert message and a second indication of the second of the plurality of types of ambient conditions to the control panel and activates the alert indicator.

2. The wearable device of claim 1 wherein the first sensor and the second sensor include at least one of an ambient light sensor, a distance sensor, an ultraviolet light sensor, or a color sensor, and wherein the first one of the plurality of types of ambient conditions and the second one of the plurality of ambient type conditions include at least one of an ambient light level, proximity of the wearable device to an object, an ultraviolet light level, or an ambient light color.

3. The wearable device of claim 1 wherein the processor determines whether the first value or the second value correspond to an operating mode of the wearable device, measures a time the wearable device is in the operating mode, and transmits the alert message to the control panel when the time exceeds a predetermined threshold.

4. The wearable device of claim 1 further comprising an alert button, wherein the processor receives a signal indicative of activation of the alert button and, responsive thereto, immediately transmits the alert message to the control panel.

5. An automation system comprising:
   a plurality of connected devices;
   a control panel coupled to each of the plurality of connected devices that adjusts a respective output of each of the plurality of connected devices at a respective location of each of the plurality of connected devices; and
   a wearable device wirelessly paired with the control panel,
   wherein the control panel receives, from the wearable device, an alert message that includes a first indication of a first type of ambient condition monitored by the wearable device or a second indication of a second type of ambient condition monitored by the wearable device that is different from the first type of ambient condition,
   wherein, responsive to receiving the alert message and the first indication of the first type of ambient condition, the control panel identifies and selects a first set of the plurality of connected devices associated with the first type of ambient condition and for which the respective location is proximate a current location of the wearable device and, responsive thereto, adjusts the respective output of each of the first set of the plurality of connected devices, and
   wherein, responsive to receiving the alert message and the second indication of the second type of ambient condition, the control panel identifies and selects a second set of the plurality of connected devices associated with the second type of ambient condition and for which the respective location is proximate the current location of the wearable device and, responsive thereto, adjusts the respective output of each of the second set of the plurality of connected devices.

6. The automation system of claim 5 wherein a processor of the wearable device receives a first value corresponding to the first type of ambient condition at the current location of the wearable device from a first sensor of the wearable device, compares the first value to a first alert condition for the first sensor stored in a first memory of the wearable device, and when the first value matches the first alert condition, transmits the alert message and the first indication of the first type of ambient condition to the control panel, and wherein the processor receives a second value corresponding to the second type of ambient condition at the current location of the wearable device from a second sensor of the wearable device, compares the second value to a second alert condition for the second sensor stored in the first memory, and when the second value matches the second alert condition, transmits the alert message and the second indication of the second type of ambient condition to the control panel.

7. The automation system of claim 6 wherein the wearable device transmits the first value or the second value to the control panel, wherein the control panel adjusts the respective output of each of the first set of the plurality of connected devices by a first specific amount calculated by comparing the first value to a first ideal level for the respective output of each of the first set the plurality of connected devices stored in a second memory of the control panel, and wherein the control panel adjusts the respective output of each of the second set of the plurality of connected devices by a second specific amount calculated by comparing the second value to a second ideal level for the respective output of each of the second set the plurality of connected devices stored in the second memory.

8. The automation system of claim 6 wherein the wearable device transmits the first value and the second value to the control panel, wherein the control panel saves the first value and the second value in a second memory of the control panel, and wherein the control panel displays an analysis of changes in the first value and the second value over time.

9. The automation system of claim 6 wherein the first sensor and the second sensor include at least one of an ambient light sensor, a distance sensor, an ultraviolet light sensor, or a color sensor, and wherein the first type of ambient condition and the second type of ambient condition include at least one of an ambient light level, proximity of the wearable device to an object, an ultraviolet light level, or an ambient light color.

10. The automation system of claim 5 wherein the control panel adjusts the respective output of each of the first set of the plurality of connected devices or each of the second set of the plurality of connected devices to produce a warning signal.

11. The automation system of claim 5 wherein the control panel activates a local alarm indicator of the control panel responsive to receiving the alert message.

12. The automation system of claim 5 wherein the control panel forwards the alert message to a mobile device wirelessly paired with the control panel.

13. The automation system of claim 12 wherein the control panel adjusts the respective output of each of the first set of the plurality of connected devices or each of the second set of the plurality of connected devices responsive to receiving user input from the mobile device.

14. The automation system of claim 5 wherein the plurality of connected devices are assigned to a plurality of zones of the automation system based on the respective location of each of the plurality of connected devices, wherein the wearable device is assigned to one of the plurality of zones, and wherein the control panel identifies the first set of the plurality of connected devices and the second set of the plurality of connected devices by identifying which of the plurality of connected devices are assigned to the one of the plurality of zones.

15. A method comprising:
a first sensor of a wearable device detecting a first value corresponding to a first type of ambient condition monitored by the wearable device at a current location of the wearable device;
a second sensor of the wearable device detecting a second value corresponding to a second type of ambient condition monitored by the wearable device at the current location of the wearable device;
responsive to a control panel receiving the first value, a first indication of the first type of ambient condition, and an alert message from the wearable device, the control panel identifying and selecting a first set of a plurality of connected devices associated with the first type of ambient condition and for which a respective location is proximate the current location of the wearable device;
responsive to the control panel receiving the second value, a second indication of the second type of ambient condition, and the alert message from the wearable device, the control panel identifying and selecting a second set of the plurality of connected devices associated with the second type of ambient condition and for which the respective location is proximate the current location of the wearable device; and
responsive to identifying the first set of the plurality of connected devices, the control panel adjusting a respective output of each of the first set of the plurality of connected devices; and
responsive to identifying the second set of the plurality of connected devices, the control panel adjusting the respective output of each of the second set of the plurality of connected devices.

16. The method of claim 15 further comprising:
a processor of the wearable device receiving the first value;
the processor comparing the first value to a first alert condition for the first sensor stored in a first memory of the wearable device;
when the first value matches the first alert condition, the processor transmitting the alert message and the first indication of the first type of ambient condition to the control panel;
the processor receiving the second value;
the processor comparing the second value to a second alert condition for the second sensor stored in the first memory; and
when the second value matches the second alert condition, the processor transmitting the alert message and the second indication of the second type of ambient condition to the control panel.

17. The method of claim 16 further comprising:
the control panel adjusting the respective output of each of the first set of the plurality of connected devices by a first specific amount calculated by comparing the first value to a first ideal level for the respective output of each of the first set of the plurality of connected devices stored in a second memory of the control panel; and
the control panel adjusting the respective output of each of the second set of the plurality of connected devices by a second specific amount calculated by comparing the second value to a second ideal level for the respective output of each of the second set of the plurality of connected devices stored in the second memory.

18. The method of claim 15 further comprising:
the control panel forwarding the alert message to a mobile device wirelessly paired with the control panel;
the control panel receiving user input from the mobile device; and
the control panel adjusting the respective output of each of the first set of the plurality of connected devices or each of the second set of the plurality of connected devices responsive to the user input.

19. The method of claim 15 further comprising:
assigning the plurality of connected devices to a plurality of zones based on the respective location of each of the plurality of connected devices;
assigning the wearable device to one of the plurality of zones; and the control panel identifying the first set of the plurality of connected devices and the second set of the plurality of connected devices by identifying which of the plurality of connected devices are assigned to the one of the plurality of zones.

20. The method of claim 15 wherein the first sensor and the second sensor include at least one of an ambient light sensor, a distance sensor, an ultraviolet light sensor, or a color sensor, and wherein the first type of ambient condition and the second type of ambient condition include at least one of an ambient light level, proximity of the wearable device to an object, an ultraviolet light level, or an ambient light color.

* * * * *